US012653442B2

(12) United States Patent
Nwulia

(10) Patent No.: US 12,653,442 B2
(45) Date of Patent: Jun. 16, 2026

(54) OLFACTORY TESTING SYSTEMS AND METHODS

(71) Applicant: Evon Medics, LLC, Ellicott City, MD (US)

(72) Inventor: Evaristus A. Nwulia, Ellicott City, MD (US)

(73) Assignee: Evon Medics, LLC, Ellicott City, MD (US)

( * ) Notice: Subject to any disclaimer, the term of this patent is extended or adjusted under 35 U.S.C. 154(b) by 570 days.

(21) Appl. No.: 18/023,603

(22) PCT Filed: Aug. 25, 2021

(86) PCT No.: PCT/US2021/047492

§ 371 (c)(1),
(2) Date: Feb. 27, 2023

(87) PCT Pub. No.: WO2022/046864

PCT Pub. Date: Mar. 3, 2022

(65) Prior Publication Data

US 2023/0309900 A1        Oct. 5, 2023

Related U.S. Application Data

(60) Provisional application No. 63/070,672, filed on Aug. 26, 2020.

(51) Int. Cl.
*A61B 5/00*        (2006.01)

(52) U.S. Cl.
CPC .......... *A61B 5/4011* (2013.01); *A61B 5/7475* (2013.01)

(58) Field of Classification Search
CPC ........................... A61B 5/4011; A61B 5/7475
See application file for complete search history.

(56) References Cited

U.S. PATENT DOCUMENTS 6,325,475 B1    12/2001    Hayes et al.
6,558,322 B1    5/2003    Busch
(Continued)

FOREIGN PATENT DOCUMENTS

WO        2006/135368 A1    12/2006
WO        2019/010172 A1    1/2019

OTHER PUBLICATIONS

Croy et al. 2009 (Year: 2009).*
(Continued)

*Primary Examiner* — Justin Xu
(74) *Attorney, Agent, or Firm* — Fitch, Even, Tabin & Flannery, LLP

(57)        ABSTRACT

Systems and methods are provided herein useful to olfactory testing. In some embodiments, the olfactory testing device comprises a cartridge having a plurality of odorant chambers, each odorant chamber housing an odorant therein. The olfactory testing device further includes a rear compartment configured to receive the cartridge and a tube in fluid communication with the outlet opening of the cartridge. In addition, the olfactory testing device includes an air pump having an outlet in fluid communication with the inlet opening of the cartridge, wherein air is supplied to one of the odorant chambers from the air pump, flows around the odorant, and exits the cavity through the tube, wherein a portion of the odorant is entrained in the air as it flows through the odorant chamber. Also provided are methods of testing odor threshold sensitivity and odor discrimination using the olfactory testing device.

5 Claims, 7 Drawing Sheets

(56) References Cited

U.S. PATENT DOCUMENTS

| | | |
|---|---|---|
| 2016/0287161 A1 | 10/2016 | Smith et al. |
| 2020/0253531 A1 | 8/2020 | Smith et al. |

OTHER PUBLICATIONS

Rumeau et al. 2016 (Year: 2016).*
Zernecke et al. 2010 (Year: 2010).*
Patent Cooperation Treaty, International Search Report and Written Opinion of the International Searching Authority dated Feb. 9, 2022 for International Application No. PCT/US2021/0474902, 12 pages.
Zhang, Jingji et al., Ultrasensitive Detection of Amines by a Trace Amine-Associated Receptor, The Journal of Neuroscience, Feb. 13, 2013, vol. 33, No. 7, pp. 3228-3239.

* cited by examiner

300

General Screening 310

COVID-19 320

Brain Injury 330

Nose Injury/Damage 340

Plenum Connection

Air Outlet

Pourous Media
Scented With Fluid

Air Inlet Airflow

Airflow

Mint

Pine

Clove

Citrus

Cinnamon

Garlic

*FIG. 5*

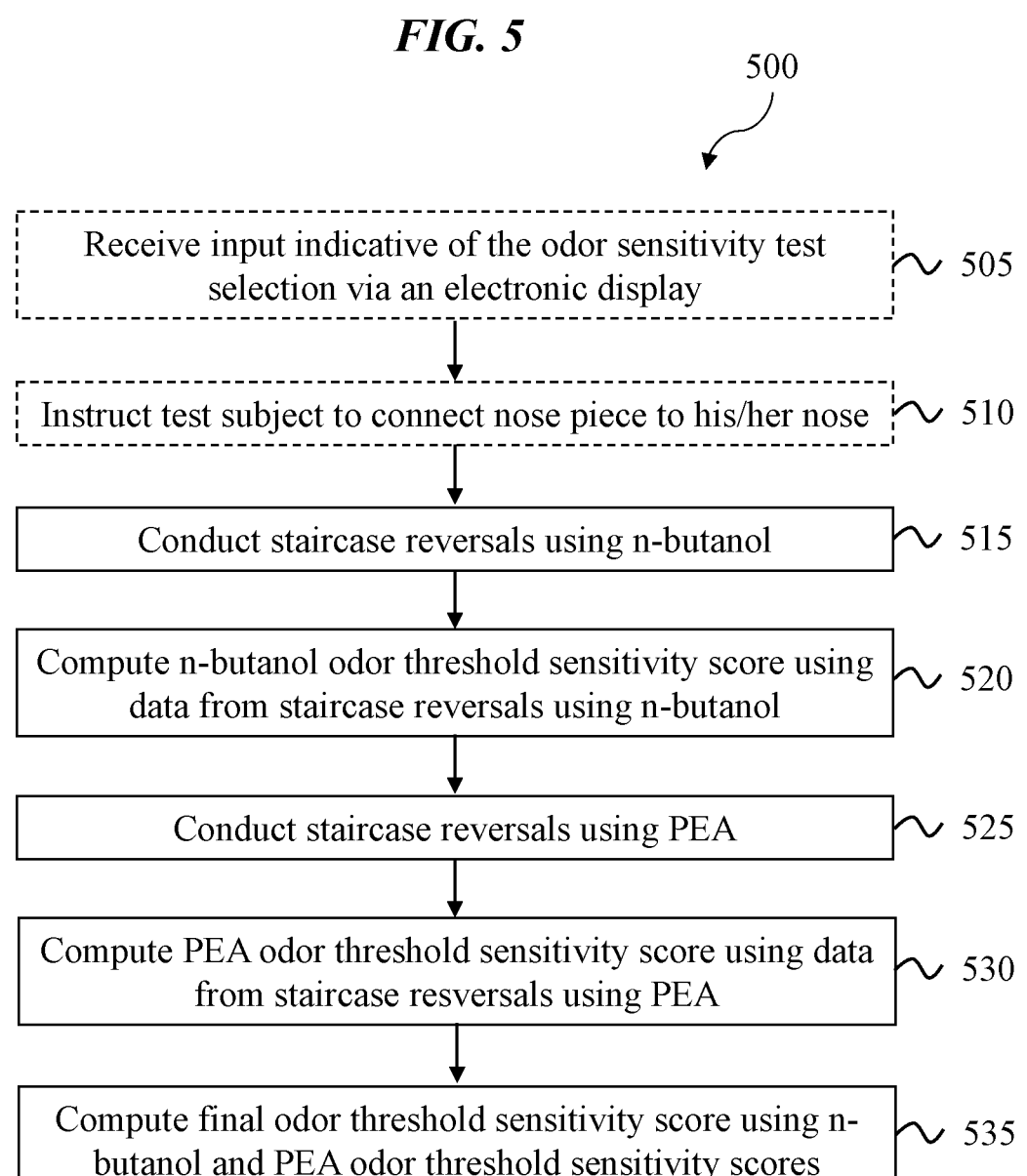

500

Receive input indicative of the odor sensitivity test selection via an electronic display — 505

Instruct test subject to connect nose piece to his/her nose — 510

Conduct staircase reversals using n-butanol — 515

Compute n-butanol odor threshold sensitivity score using data from staircase reversals using n-butanol — 520

Conduct staircase reversals using PEA — 525

Compute PEA odor threshold sensitivity score using data from staircase resversals using PEA — 530

Compute final odor threshold sensitivity score using n-butanol and PEA odor threshold sensitivity scores — 535

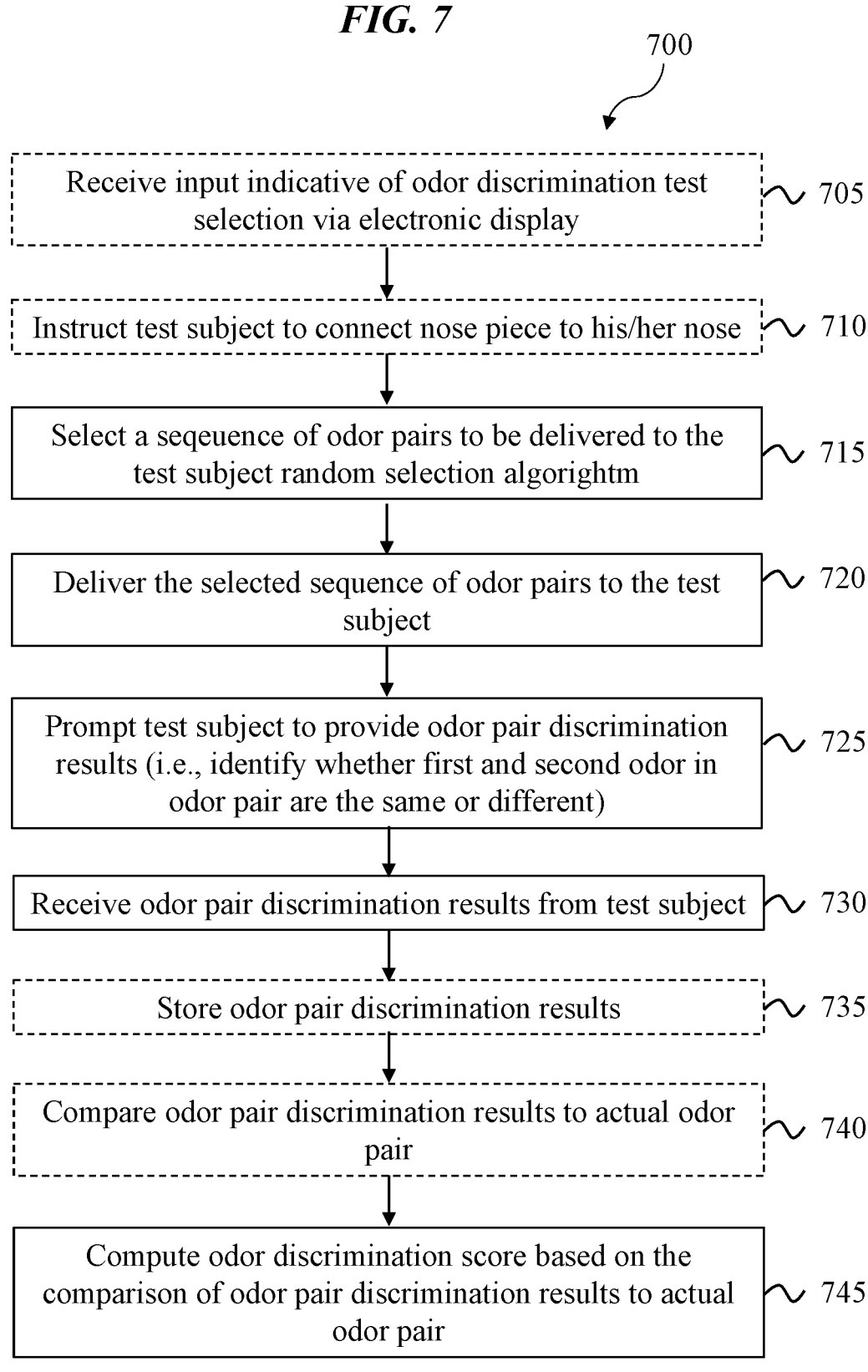

Receive input indicative of odor discrimination test selection via electronic display ⟿ 705

Instruct test subject to connect nose piece to his/her nose ⟿ 710

Select a seqeuence of odor pairs to be delivered to the test subject random selection algorightm ⟿ 715

Deliver the selected sequence of odor pairs to the test subject ⟿ 720

Prompt test subject to provide odor pair discrimination results (i.e., identify whether first and second odor in odor pair are the same or different) ⟿ 725

Receive odor pair discrimination results from test subject ⟿ 730

Store odor pair discrimination results ⟿ 735

Compare odor pair discrimination results to actual odor pair ⟿ 740

Compute odor discrimination score based on the comparison of odor pair discrimination results to actual odor pair ⟿ 745

OLFACTORY TESTING SYSTEMS AND METHODS

CROSS-REFERENCE TO RELATED APPLICATIONS

This application is a U.S. national phase application filed under 35 U.S.C. § 371 of International Application Number PCT/US2021/047492, filed Aug. 25, 2021, designating the United States which claims benefit of U.S. Provisional Application No. 63/070,672, filed on Aug. 26, 2020, which are hereby incorporated herein by reference in their entirety.

TECHNICAL FIELD

This application relates generally to systems and methods for olfactory testing.

BACKGROUND

The olfactory system consists of nerves and nervous system tissues that enable a person to perceive and process smells. The olfactory system is divided into the peripheral olfactory system and the central olfactory system. The peripheral olfactory system includes nervous tissues in the nose (called olfactory neuroepithelium) and the olfactory bulb, which is the first part of the brain that receives the neurons from the nose. The peripheral olfactory system (in the nose and olfactory bulb) enables a person to perceive and to discriminate smells. Toxins such SARS-COV2 (the virus causing COVID-19), herpes viruses, and other toxins may enter the olfactory neuroepithelium and damage the peripheral olfactory system, leading to impairment in smell perception. When the damage is profound, there is complete loss of smell (known as anosmia). When a person has anosmia, the person is eventually unable to perform higher odor functions, such as the identification of odors or odor memory. In addition, some people only suffer minor loss of odor sensitivity (known as hyposmia) and may still be able to have unimpaired odor identification or odor memory, since the virus or toxins affect only the periphery. For example, individuals who would eventually develop anosmia from COVID-19 may have only have mild hyposmia in early stages of the viral infection.

Olfactometers are devices used to test such impairments in the functioning of the olfactory neuroepithelium in the nose and in the olfactory bulb. Olfactometers may be used to test odor threshold sensitivity and odor discrimination for a subject. In olfactometers, oil-based odorants, for example, housed in bottles to produce aromas in a controlled manner and conduct olfactory tests. Diluents such as mineral oils are often used as a carrier for the odorants and as a neutral control for odorants in olfactometers. Oil-based odorants used in olfactometers may leave oil residues in tubing carrying the oil between parts of the device and into the subject's nose. These oil residues may confound olfactory test results. Additionally, olfactometers may be bulky and complex and, accordingly, not particularly suitable for portable or over-the-counter solutions for olfactory testing.

BRIEF DESCRIPTION OF THE DRAWINGS

Disclosed herein are embodiments of systems, apparatuses, and methods for olfactory testing. This description includes drawings, wherein:

FIG. 5 is process flow diagram in accordance with some embodiments.

FIG. 7 is process flow diagram in accordance with some embodiments.

Figure 1A:
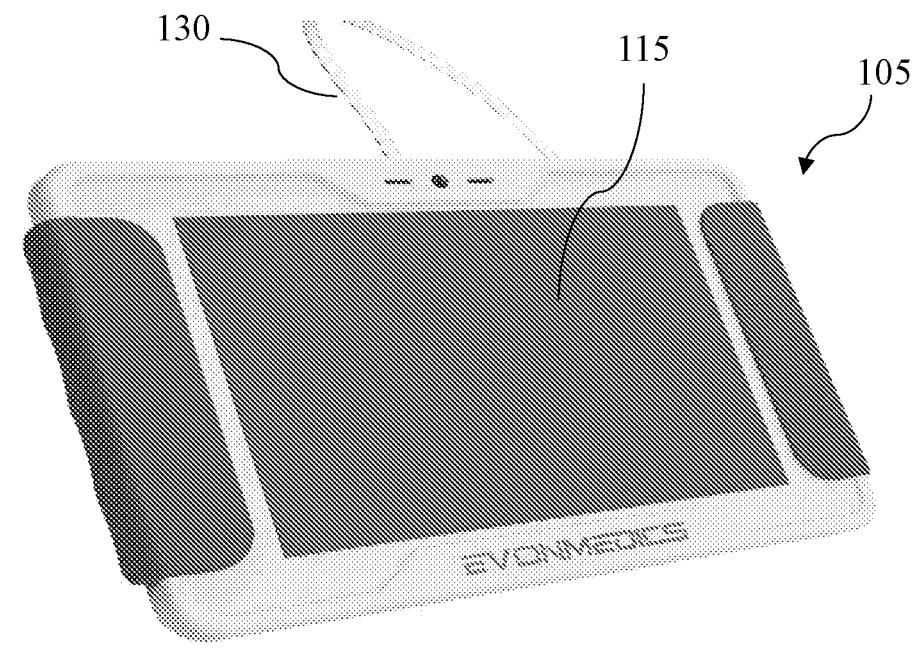
FIG. 1A is front perspective view in accordance with some embodiments.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, systems, apparatuses and methods are provided herein useful to olfactory testing. The olfactory testing device includes a cartridge that houses one or more odorants and delivers odorized stimuli to a test subject as part of an olfactory testing protocol. In operation, air passes through the cartridge of the olfactory testing device to produce an odorized stimulus, which comprises odorant molecules entrained in air. The odorized stimulus is delivered to the test subject via a tube on the olfactory testing device. The olfactory testing device may further include an electronic screen with a user interface through which the test subject may input information pertaining to the odorized stimulus. In some embodiments, the olfactory testing protocol may be a rapid result test for odor function, such as an odor threshold sensitivity test and an odor discrimination test.

In some embodiments, the olfactory testing device comprises a cartridge comprising an inlet opening, an outlet opening, and a cavity therebetween, the cavity including a plurality of odorant chambers, each odorant chamber housing an odorant therein. The olfactory testing device further includes a rear compartment configured to receive the cartridge and a tube in fluid communication with the outlet opening of the cartridge. In addition, the olfactory testing device includes an air pump having an outlet in fluid communication with the inlet opening of the cartridge, wherein air is supplied to one of the odorant chambers from the air pump via the inlet opening, flows around the odorant, and exits the cavity through the tube via the outlet opening, wherein a portion of the odorant is entrained in the air as it flows through the odorant chamber and is delivered to the test subject via the tube.

In some embodiments, a method of testing the odor threshold sensitivity of a test subject includes conducting staircase reversals (see FIG. 6) using n-butanol and computing an n-butanol odor threshold sensitivity score using data from the staircase reversals using n-butanol. The method further includes conducting staircase reversals using phenylethylamine and computing a phenylethylamine odor threshold sensitivity score using data from the staircase reversals using phenylethylamine. In addition, the method includes computing a final odor threshold sensitivity score using the n-butanol odor threshold sensitivity score and the phenylethylamine odor threshold sensitivity score, wherein the final odor threshold sensitivity score is the mean of the n-butanol and phenylethylamine odor threshold sensitivity scores.

In some approaches, the staircase reversals using n-butanol or phenylethylamine include delivering a first pair of stimuli including a first neutral air stimulus and a first odorized air stimulus comprising n-butanol or phenylethylamine and prompting the test subject to indicate which stimulus in the first pair is stronger. Where the test subject correctly indicates which stimulus in the first pair is stronger, the method includes delivering a second pair of stimuli including a second neutral air stimulus and a second odorized air stimulus comprising n-butanol or phenylethylamine, wherein the second odorized air stimulus has a lower odor intensity of n-butanol or phenylethylamine than the first odorized stimulus. Next, the method includes prompting the test subject to indicate which stimulus in the second pair is stronger. Where the test subject does not correctly indicate which stimulus in the second pair is stronger, the method includes delivering a third pair of stimuli including a third neutral air stimulus and a third odorized air stimulus comprising n-butanol or phenylethylamine, wherein the third odorized air stimulus has a higher odor intensity of n-butanol or phenylethylamine than the second odorized stimulus.

In some approaches, a method of testing the odor discrimination of a test subject includes selecting a sequence of odor pairs to be delivered to the test subject using a random selection algorithm and delivering the selected sequence of odor pairs to the test subject. After each odor pair is delivered to the test subject, the method includes prompting the test subject to identify whether the odors in the odor pair are the same or different, and receiving input from the test subject indicative of whether the odors in the odor pair are the same or different. The method further includes comparing the input from the test subject to the actual odor pair and computing an odor discrimination score based on the comparison.

Figure 1B:
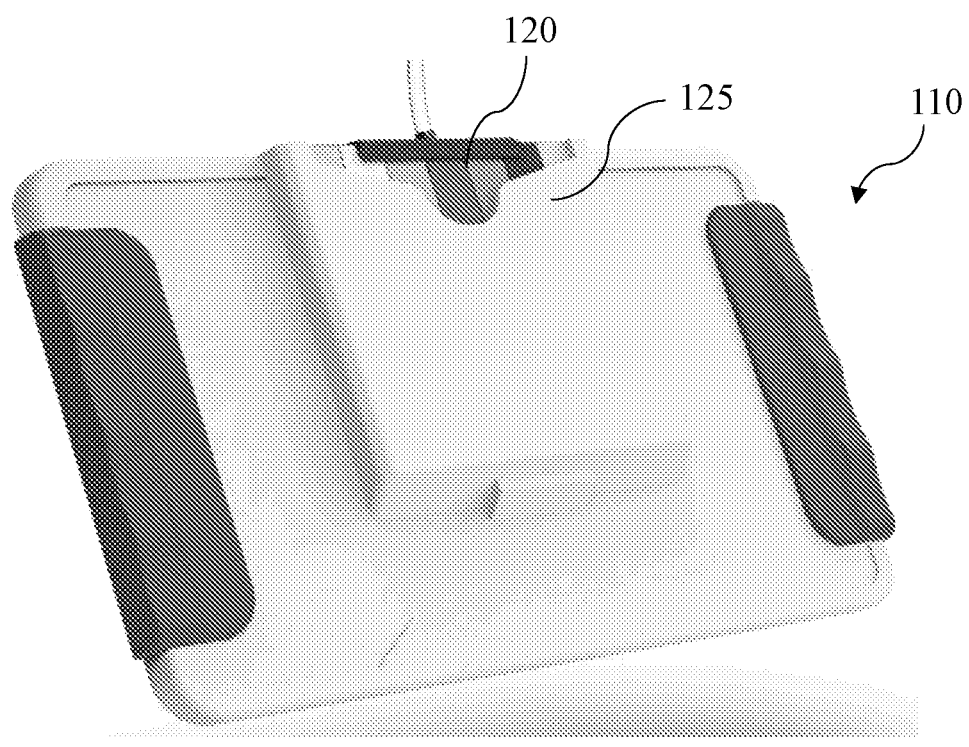
FIG. 1B is a rear perspective view of the form shown in FIG. 1A.

FIG. 1 includes a schematic diagram of an olfactory testing device in accordance with some embodiments. FIG. 1 illustrates the front 105 of the olfactory testing device and the back 110 of the olfactory testing device. In some forms, the device of FIG. 1 is handheld and portable. The device may be built in various small forms, including but not limited to, a handheld tablet, a hip pack, or an augmented reality/virtual reality (AR/VR) headset.

With reference to FIG. 1, the olfactory testing device includes an electronic display 115, an odorant cartridge 120 housing one or more odorants, a rear compartment 125 configured to receive the odorant cartridge 120, and a tube 130 for delivering the odorant(s) from the cartridge to a test subject or other user of the device.

Figure 3:
FIG. 3 is a schematic diagram in accordance with some embodiments.

The electronic display 115 may include a user interface through which a test subject may input information into the olfactory testing device or make selections. The user interface, for example, may be a touch screen. A test subject may input information into the olfactory testing system via the user interface. For example, the user may select among various programs or testing protocols to be implemented by the olfactory testing device. In addition, the test subject may input information such as other symptoms, biographical information (e.g., age, gender, ethnicity), make selections, or provide answers via the user interface. In one example, the test subject may input information on presence or absence of systemic body symptoms (including but not limited to fever, cough, sore throat, fatigue, diarrhea, loss of taste, loss of appetite). Information may also be presented to a test subject via the electronic display 115. Such information may include, for example, testing instructions, prompts, results, questions, or selection options. In one example, results information may be presented to a test subject in the form of raw and normative scores on odor sensitivity and odor discrimination tests, by age, sex, ethnicity, and other demographic variables. An exemplary user interface for the electronic display 115 is depicted in FIG. 3.

Figure 4A:
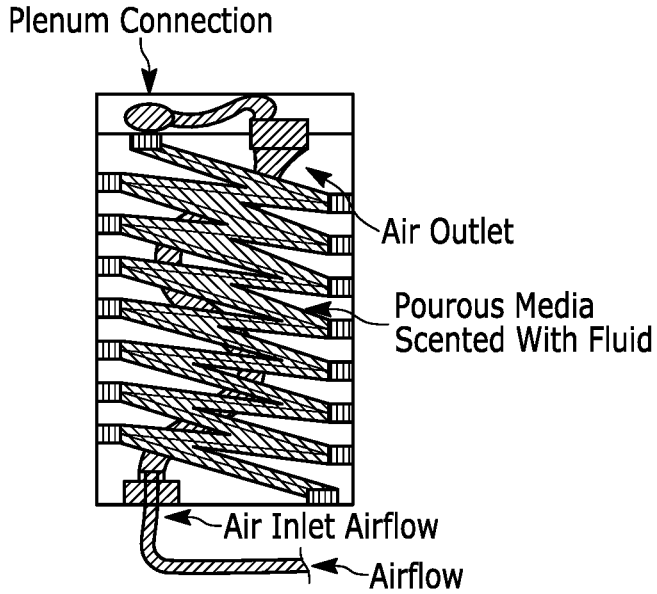
FIG. 4A is a schematic diagram in accordance with some embodiments.

The odorant cartridge 120 of the olfactory testing device may include one or more odorants. In some forms, the cartridge 120 of the olfactory testing device may include one or more odorant chambers, each odorant chamber housing an odorant. The cartridge 120 may include any suitable number of odorants. In some forms, the cartridge 120 may include about 1-20 odorants, about 1-10 odorants, or about 1-5 odorants. Odorants may include one or more of vanillin, eucalyptol, Limonene, lavendulol, cinnamaldehyde, isoamyl acetate, menthol, citral, allyl valerate, and thymol. The cartridge 120 may be a liquid jet cartridge or an evaporative cartridge. In some forms, the cartridge may refillable or reusable and, in other forms, the cartridge may be disposable. An exemplary evaporative odorant cartridge 120 is depicted in FIG. 4A. The cartridge may be easily inserted or removed by a user, for example, inserted into or removed from the rear compartment 125 using only manual force or pressure or without the use of tools.

In some embodiments, in operation, a test subject selects an olfactory testing protocol via the electronic display 115. The olfactory testing protocol may involve delivering one or more stimuli to the test subject. To deliver an odorized stimulus, the olfactory testing device receives neutral air from the ambient environment. The neutral air passes through cartridge 120, picking up odorant stored within, and is delivered to the test subject via the tube 130. In some approaches, the air passing through the cartridge 120 is odorized to produce an odorized stimulus. In other approaches, neutral air may pass through the cartridge 120 un-odorized to produce a neutral or blank stimulus. After delivering the stimulus to the test subject, the olfactory testing device may prompt the test subject to input information via the user interface on the electronic display 115. Such information may include information regarding detection or identification of the odorant. In this manner, the olfactory testing device may collect information required from the test subject as part of the olfactory testing protocol. The olfactory testing device may further present information, test results, questions, or information to the test subject via the electronic display 115.

Figure 2:
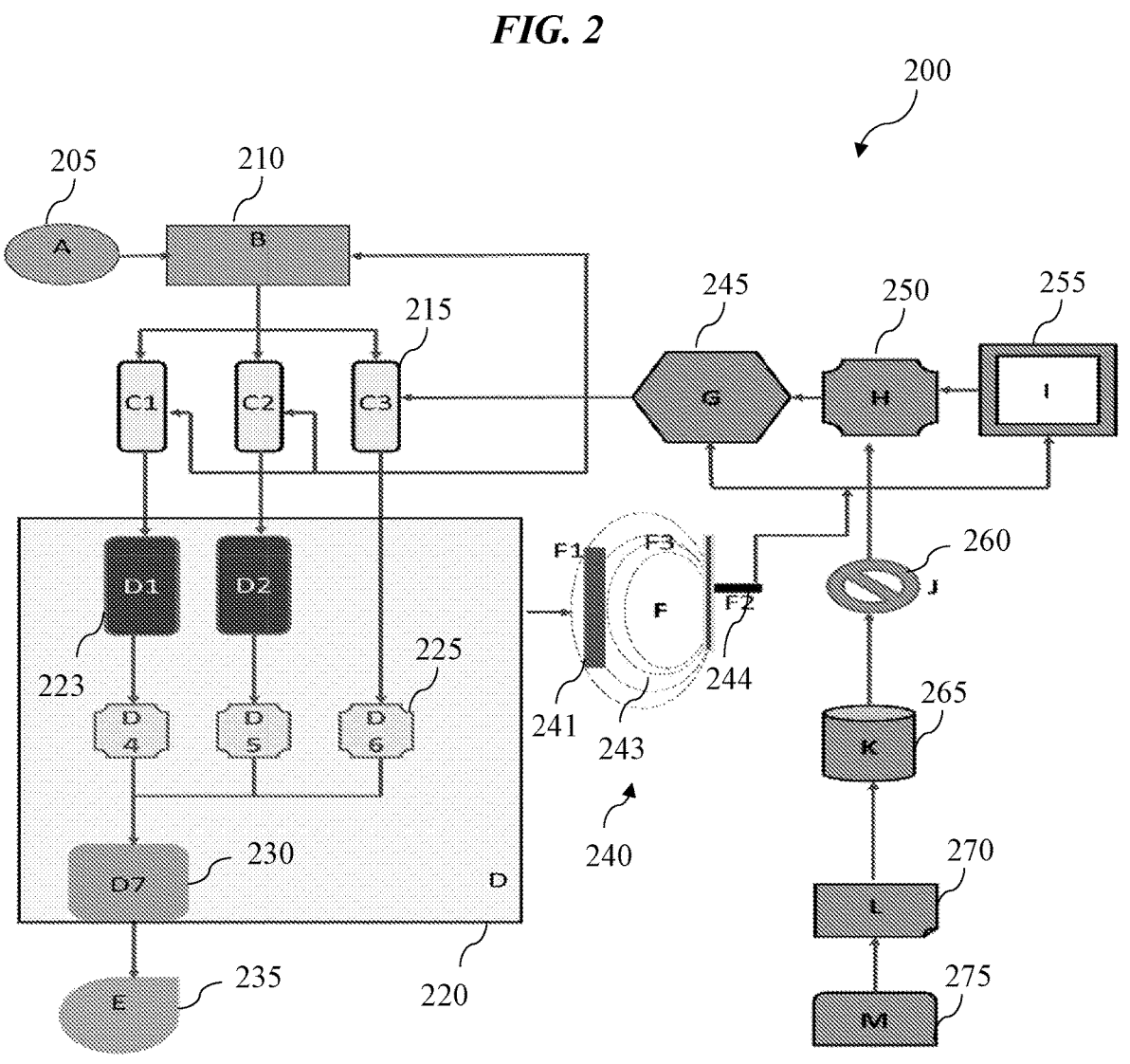
FIG. 2 is schematic diagram in accordance with some embodiments.

FIG. 2 includes a schematic diagram of the olfactory testing device 200 in accordance with some embodiments. The olfactory testing device 200 includes a pneumatic system and an electrical system. The pneumatic system supplies the air from the ambient environment to the olfactory testing device and delivers stimuli comprising air to a test subject. The electrical system interfaces with the pneumatic system to control components of the pneumatic system and to analyze stimuli produced by the pneumatic system.

The pneumatic system of the olfactory testing device 200 includes a filter 205, a pump 210, solenoid valves 215, a cartridge 220, and a disposable cannula 235. The cartridge 220 includes odorant chambers 223, check valves 225, and a cannula barb 230. In the pneumatic system, the filter 205 is positioned upstream of the pump 210. Three solenoid valves 215 are positioned on conduits downstream of the pump 210 and control the supply of air through the cartridge 220. Two odorant chambers 223 are housed within the cartridge 220 and receive air from the outlet of the pump 210. An odorant is housed within each odorant chamber 223. A check valve 225 is positioned at the outlet of each odorant chamber 223. The check valves 225 may help to prevent the flow of odorized air back into the odorant chamber 223. In addition, the check valves 225 help to prevent contamination of components in the pneumatic system that are upstream of the check valves 225. In addition, the cartridge includes a neutral air conduit that bypasses the odorant chambers 223. This neutral air conduit receives air from the outlet of the pump 210 and also includes a check valve 225. The conduits at the outlet of each odorant chambers 223 and the neutral air conduit tie into a common header which connects to an outlet opening of the cartridge 220. In some forms, each component downstream of the check valves 225 is replaceable, for example, to prevent contamination when the olfactory testing device is used between different test subjects. The cannula barb 230 may be a one-pierce fitting that will connect with and supply air. The cannula barb 230 feeds a tube connected to the cannula 235. In some forms, the cannula 230 and the cannula 235 are disposable to prevent contamination between test subjects.

In operation, the pneumatic system of the olfactory testing device 200 receives neutral air from the ambient environment. Incoming neutral air passes through the air filter 205 and is pumped through the cartridge 220 by the air pump 210. In some approaches, the air pump 210 may be capable of generating an air flow rate of between about 0.5 liters/minute and about 6 liters/minute. Solenoid valves 215 control the flow of air through the cartridge 220. For example, opening the solenoid valve 215 upstream of an odorant chamber 223 allows neutral air to pass through the odorant chamber and around the odorant stored therein. Thus, odorant molecules are entrained in the neutral air as it passes through the odorant chambers 223 to produce odorized air (i.e., an odorized stimulus). Fine vaporized liquid droplets may be entrained in the air leaving the cartridge. Varying the volume of air drawn through the odorant chambers 223 by the air pump 210 controls the intensity of the odorized air. That is the device may bias the amount of odorant entrained in the air and drawn from the cartridge by varying the flow rate of air through the cartridge. The check valves 225 at the outlet of the odorant chambers 223 help to prevents the flow of odorized air back into the odorant chamber. Opening the solenoid valve on the neutral air conduit allows neutral air to bypass the odorant chambers 223 and flow through the check valve 225 and out of the cartridge 220 un-odorized (i.e., a neutral stimulus). Odorized or neutral air exits the cartridge 220 via the cannula barb 230 and through a tube. The tube ties into the disposable cannula 235, which may be placed into, on, or near the nose of a test subject to deliver a stimulus to the test subject.

The electrical system of the olfactory testing device 200 may include a radio frequency identification (RFID) system 240, power drivers 245, a microcontroller 250, a touch screen 255, a power switch 260, a battery system 265, a charger port 270, and an external charger 275. The RFID system 240 further includes a sensor 241, a magnetic field 243, and a pick-up coil 244.

In operation, the power drivers 245 supplies power to the olfactory testing device. The micro controller 250 in the electrical system is in communication with other components of the electrical system and runs a number of built-in software programs or testing protocols. The test subject may communicate with the micro-controller via the touch screen 255. Through the touch screen 255, for example, the test subject may select a particular program or testing protocol to be carried out by the device. Testing protocols may deliver one or more stimuli to the test subject via the pneumatic system of the olfactory testing device. The RFID system 240 may automatically recognize the odorants included in the inserted cartridge. The RFID system 240 may store memory of odor types and intensities while the user is receiving smells and answering questions about the stimuli presented via the pneumatic system. In one example, the RFID system 240 may read an RFID tag on the cartridge 220 that is inserted in the device, automatically identify odorants housed within the cartridge 200. A magnetic field 243 is generated between pick-up coil 244 and the sensor 241 of the RFID system 240. In another example, the RFID system 240 may act as a sensor for automatic recognition of particular odors and of the intensity of odors being dispersed. The RFID system 240 may sense the type of odor and the intensity (or concentration) of odorant being dispersed to a user, for example, during a testing protocol (e.g., an odor sensitivity or discrimination test). Changes in the dielectric properties of the air carrying the odorants are sensed by the RFID system 240, which is in communication with the conduit of the air outflow from the cartridge 220. Odorants and varying intensity of odor smell produce changes dielectric properties of the odorant airflow. The RFID system 250 monitors the change in the dielectric constant of the airflow contents as a function of storage time by taking advantage of the electromagnetic field penetration depth out of plane relative to the system and performing analysis directly through the contact medium.

Further, in operation the test subject may input information to the olfactory testing device via the touch screen 255 before, during, and/or after the test subject receives the odor stimulus. The touch screen 255 includes a user interface through which a test subject may input information that pertains to the testing protocol. For example, a test subject may input information regarding odor name and intensity via the touch screen as part of a testing protocol. Automatic determinations of the odorants and their intensity by the RFID system 240 may be further performed and registered in the system, which may then be used to compare against the user's selection of the odorant names and intensities.

In some embodiments, the automatic recognition of odors and their intensities in the olfactory testing device may also be accomplished by sensors for electronic noses including but not limited to: metal-oxide-semiconductor (MOSFET) devices, which works on the principle that molecules entering the sensor area will be charged either positively or negatively, which have a direct effect on the electric field inside the MOSFET; organic polymers that conduct electricity; polymer composites, which are similar to conducting polymers but formulated of non-conducting polymers with the addition of conducting material such as carbon black;

quartz crystal microbalance, which is an approach for measuring mass per unit area by measuring the change in frequency of a quartz crystal resonator; and surface acoustic wave (SAW), which is a class of microelectromechanical systems that rely on the modulation of surface acoustic waves to sense a physical phenomenon.

The power switch 260, battery system 265, charger port 270, and external charger 275 in the electrical system supply electrical power to the device. These components facilitate the portability for the olfactory testing device, whether for home- or field-testing operations.

In some forms, the olfactory testing device of FIG. 2 may be portable and handheld. Using a cartridge, for example as opposed to a plurality of bottles, to house a plurality of odorants may facilitate the portability of the device. It is contemplated that using air versus mineral oil bias the dilution of the odorant used in the testing device may reduce the build-up of residues within the device, which may confound results.

FIG. 3 includes a schematic diagram of an exemplary user interface 300 of the olfactory testing device in accordance with some embodiments. The user interface 300 is included on the electronic display of the olfactory testing device. The exemplary user interface includes four icons representing testing options that may be selected by a test subject. The icons on the user interface 300 include a general screening 310, a COVID-19 screening 320, a brain injury screening 220, and a nose injury/damage screening 340. In some embodiments, after a test subject selects the general screening 310 icon, the user interface 300 presents two additional icons representing testing options for both odor threshold sensitivity and odor discrimination tests.

Figure 4B:
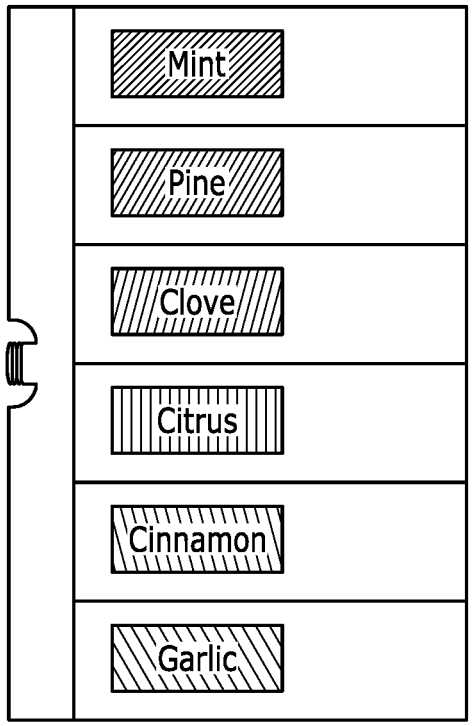
FIG. 4B is a schematic diagram in accordance with some embodiments.

FIG. 4A includes a schematic diagram of an exemplary cartridge for the olfactory testing system in accordance with some embodiments. The cartridge depicted in FIG. 4A is an evaporative cartridge that houses a plurality of odorants. The cartridge includes an inlet opening, an outlet opening, and an inner cavity disposed therebetween. The inlet opening of the cartridge is in fluid communication with an air supply. The cartridge further includes a plenum connection in fluid communication with the outlet opening and the inner cavity of the cartridge. Odorants are housed within the inner cavity of the cartridge. As discussed above, the inner cavity of the cartridge may be divided into one or more odorant chambers, each of which houses a separate odorant. In some approaches the inner cavity of the cartridge may include between about 1-20, about 1-10, about 2-8, or about 3-7 odorant chambers. In some approaches, the cartridge may be designed to have a certain number of odorant chambers in order to administer particular olfactory tests. For example, 2 odorants (i.e., 2 odorant chambers) may be required to administer an odor threshold sensitivity test and 3 odorants (i.e., 3 odorant chambers) may be required to administer an odor discrimination test. In the exemplary cartridge of FIG. 4B, the cartridge includes 6 odorant chambers, each housing a distinct odorant.

In some forms, the odorant chambers include a porous media with an odorant. The porous media may include a layer of carbon foam with a combination of inter-connected and dead-end pores with a high lipophilicity surface adjacent to a layer of expanded graphite. The porous media may facilitate a dispersal method analogous to the dispersal wick in a candle in which odorant vapors are dispersed in air flowing out of the cartridge. Prespecified amounts of respective odorants (e.g., 4% PEA, 4% n-butanol) may be distributed on the layer of porous foam. Not wishing to be bound by theory, it is contemplated that lipophilic pores in which the odorant is distributed provide capillary forces to enable presser generated from the pressurized airflow through the cartridge to transport a mixture of air and odorants (i.e., an odorized stimulus) to the top surface of the cartridge for evaporation. That is, the porous media may provide capillary spaces that enable pressurized air to push the odorant to the top of the cartridge so it can be evaporated and distributed into the air. In some forms, the porous media may be biodegradable. It is contemplated that including a porous media as a carrier for vaporized odorants mixed with air as a diluent, as opposed to a mineral oil, may help prevent the build-up of oils within the device. In some alternative embodiments, a gas canister or aerosolized liquid method may be used to distribute or diffuse odorants.

The odorants housed within the odorant chambers may include, for example, one or more of n-butanol, phenylethylamine, vanillin, eucalyptol, Limonene, lavendulol, cinnamaldehyde, isoamyl acetate, menthol, citral, allyl valerate, and thymol. The odorant may be in solid, liquid, or gaseous form. For example, when the cartridge is a liquid jet cartridge the odorant may be in liquid form before being vaporized. In another example, when the cartridge is an evaporative cartridge, the odorant may be either in solid or liquid form before being vaporized.

In operation, air is supplied to cartridge through the inlet opening. Air passes through the inner cavity, entraining odorant molecules. Odorized air leaves the inner cavity of the cartridge via the outlet opening and passes through the plenum connection. In some forms, tubing is connected to the plenum connection. The tubing may deliver the odorized air to a test subject, for example, via a nasal cannula connected to an outlet end of the tubing.

In some forms, the olfactory testing device, cartridges, and supporting programs or software may be included in a single unit. It is contemplated that the olfactory testing device and one or more odorant cartridges compatible with the olfactory testing device may be sold as part of a kit. It is also contemplated that the cartridge and one or more odorant refills for the cartridge may be sold as part of a kit.

A number of olfactory test protocols may be conducted on a test subject using the olfactory testing device described herein. Such testing protocols may be rapid-result tests that provide a quantitative or qualitative olfactory test result in a number of minutes, for example, within about 1-15 minutes, about 1-10 minutes, about 2-8 minutes, or about 1-5 minutes. Testing protocols conducted using the olfactory testing device include, for example, odor sensitive threshold tests, odor discrimination tests, and odor identification and memory tests. The testing protocols may be conducted using only the olfactory testing device. In some approaches, the testing protocols may be conducted using both the olfactory testing device and an electronic user device such as a smart phone, personal computer, tablet, etc. (i.e., supporting software may operate on both the olfactory testing device and an electronic user device). For example, the test subject may receive stimuli via the olfactory testing device and input information or make selections via an electronic user device.

FIG. 5 is a process flow diagram for an exemplary odor sensitivity threshold test. The odor threshold sensitivity test 500 may be performed using the olfactory testing device of FIG. 2. The odor threshold sensitivity test 500 incorporates two olfactory stimulants: n-butanol and phenylethylamine (PEA) to detect changes in olfactory sensitivity. With reference to FIG. 5, the odor sensitivity threshold test 500 may begin when the olfactory testing device receives 505 an input indicative of the odor sensitivity test selection. The olfactory testing device may receive the input, for example, via a user interface of the olfactory testing device. In some approaches, a test subject may select the odor sensitivity threshold test 500 by pressing a button on a touch screen.

Next, the olfactory testing device may instruct 510 the test subject to connect a nose piece of the olfactory testing device to his or her nose. In some approaches, the olfactory testing device instructs 510 the test subject via a message presented via the user interface on the electronic display of the olfactory testing device.

The olfactory testing device then conducts 515 staircase reversals using n-butanol (i.e., an odor sensitivity test using n-butanol). The n-butanol, for example, may be housed in the cartridge of the olfactory testing device and delivered to the nose of the test subject via tubing of olfactory testing device. The staircase reversals are conducted as described with reference FIG. 6. The olfactory testing device then computes 520 an n-butanol odor threshold sensitivity score using data from the staircase reversals using n-butanol. In some approaches, the n-butanol odor sensitivity threshold score may be calculated as the mean of the last two reversals (i.e., the n-butanol or PEA concentration at which the intensity "reverses").

Next, the olfactory testing device conducts 525 staircase reversals using PEA. The PEA, for example, may be housed in the cartridge of the olfactory testing device and delivered to the nose of the test subject via tubing of the olfactory testing device. The staircase reversals are conducted as described with reference FIG. 6, however, rather than using n-butanol as the odor stimulus, the olfactory testing devices uses PEA. The olfactory testing device then computes 530 a PEA odor threshold sensitivity score using data from the staircase reversals using PEA. In some approaches, the PEA odor sensitivity threshold score may be calculated as the mean of the last two reversals using PEA.

The olfactory testing device then computes 535 a final odor threshold sensitivity score using the n-butanol and PEA odor sensitivity scores from the double staircase reversals. In some approaches, the final odor threshold sensitivity score may be a mean of the n-butanol and PEA odor sensitivity scores.

Optionally, after computation of the final odor threshold sensitivity score, the olfactory testing device may present the score or other test results to the test subject via the electronic display of the olfactory testing device. In one example, results information may be presented to a test subject in the form of raw and normative scores on odor sensitivity, by age, sex, ethnicity, and other demographic variables.

In some approaches, during the staircase reversals, each odor stimulus and neutral stimulus may be presented to the test subject for about 1-20 seconds, for about 1-10 seconds, or for about 5 seconds. Thus, the duration of the odor threshold sensitivity test administration and computation of results may take between about 1-15 minutes, about 1-10 minutes, or about 2-8 minutes. The duration of the test administration may depend on the odor perception of the test subject.

It is contemplated that administering "double" staircase reversals in this manner, using both n-butanol and PEA, may improve the opportunity to detect the loss to olfactory function. Not wishing to be bound by theory, it is believed that damage to olfactory sensitivity neurons may not be uniformly distributed among cells in the nose. Certain test subjects may lose sensitivity to n-butanol and other test subjects may lose sensitivity to PEA. Thus, conducting odor sensitivity tests using both n-butanol and PEA may improve the likelihood of detecting damage to olfactory sensitivity neurons.

Figure 6:
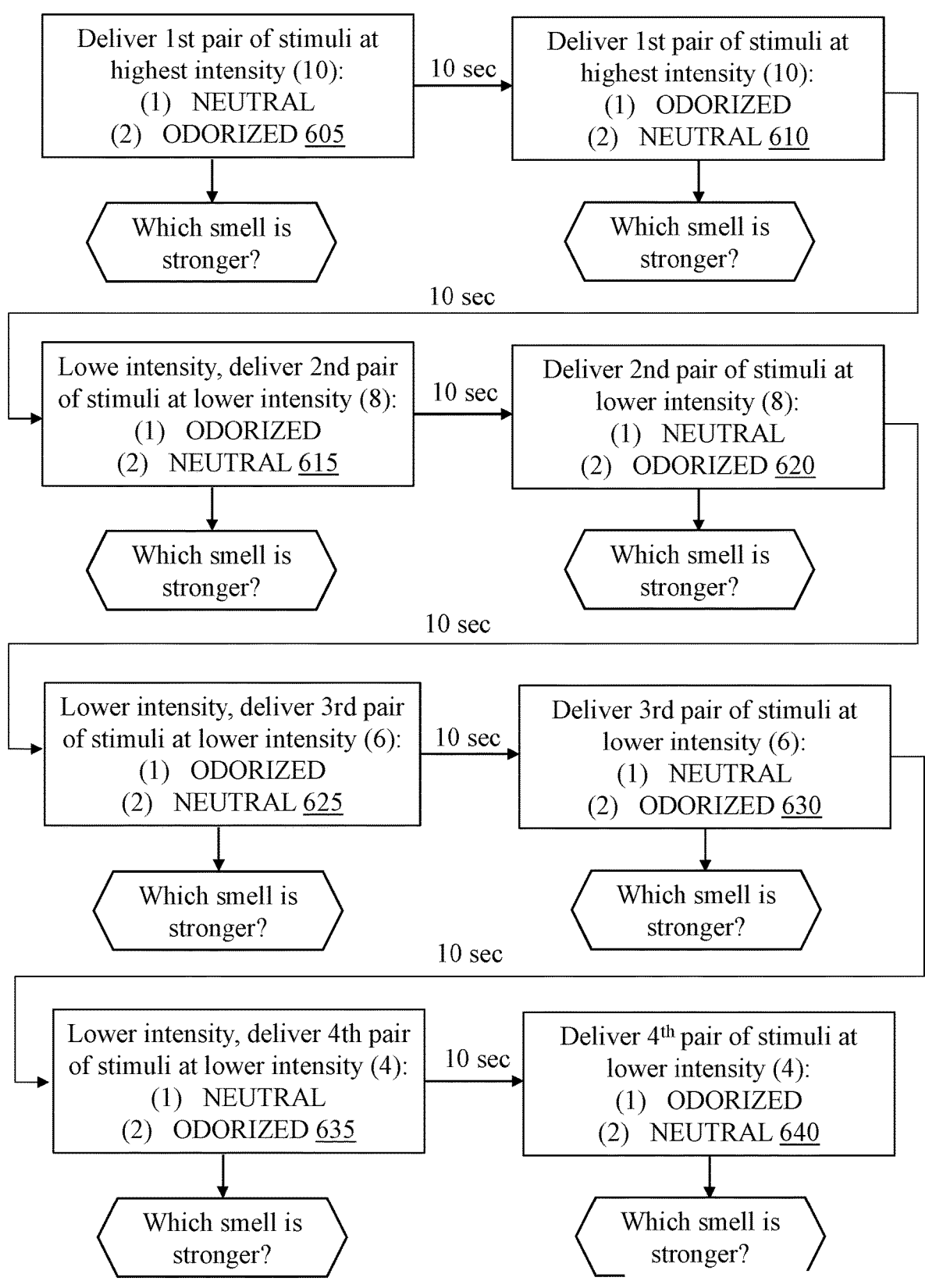
FIG. 6 is process flow diagram in accordance with some embodiments.

FIG. 6. Is a process flow diagram detailing the staircase reversal using n-butanol in the odor threshold sensitivity test of FIG. 5. An identical methodology is used to carry out the staircase reversals using PEA in the testing protocol of FIG. 5.

The staircase reversals start by delivering 610 a first pair of stimuli to a test subject. The stimuli may be a puff of air delivered by the olfactory testing device via the air pump. The first pair of stimuli includes one odorized stimulus with a predetermined intensity of n-butanol and one neutral stimulus (i.e., with un-odorized ambient environmental air). The odorized stimulus comprises n-butanol as an odorant. However, it is contemplated that the odorized stimuli discussed with reference to FIG. 6 may also include PEA as an odorant. The neutral or blank stimulus may be delivered either before or after the odorized stimulus. After delivering the first pair of stimuli, the olfactory testing device prompts the test subject to indicate which stimulus of the first pair was stronger. If a person accurately identifies which odor (i.e., the odorized stimulus or the neutral stimulus) is stronger, that same odorant pair is delivered 610 to the test subject a second time. Again, the test subject is prompted to indicate which stimulus of the pair was stronger.

If the stronger stimulant is again correctly identified, second pair of stimuli are delivered 615 to the test subject. The second pair of stimuli includes one odorized stimulus having a weaker intensity of n-butanol (i.e., weaker than the intensity of the odorized stimuli delivered in steps 605, 610) and one neutral stimulus. After delivering the second pair of stimuli, the olfactory testing device prompts the test subject to indicate which stimulus in the second pair was stronger. If the test subject incorrectly identifies which is stronger (i.e., if the person says that the neutral stimulus has a stronger smell than the odorized stimulus), the next pair of odorized stimuli delivered has a higher intensity of n-butanol. This process of reverting back to a more intense odorized stimuli is known as reversal. Subsequent reductions in the intensity of the odorize stimulus and prompts occur until the test subject is unable correctly identify which stimulus is stronger, at which point the staircase reverses and intensity of the odor stimulus is increased until the test subject correctly identifies the odorized stimulus. This process will continue for up to four reversals (see 615-640) before terminating. Accordingly, the test subject must have supplied one wrong answer followed by two subsequent right answers a total of five times for the odor threshold sensitivity test to terminate. The odor threshold sensitivity score from such reversals is the arithmetic mean of the last two reversals.

If the user correctly identifies which stimulus in the second pair is stronger at step 615 (i.e., the odor stimulus or neutral stimulus), that same odorant pair is delivered 620 to the test subject a second time. Again, the test subject is prompted to indicate which stimulus of the pair was stronger.

If the stronger stimulant is again correctly identified, a third pair of stimuli are delivered 625 to the test subject. The third pair of stimuli includes one odorized stimulus having a weaker intensity of n-butanol (i.e., weaker than the intensity of the odorized stimuli delivered at steps 615, 620) and one neutral stimulus. After delivering the third pair of stimuli, the olfactory testing device prompts the test subject to indicate which stimulus of the pair was stronger. If the user correctly identifies which stimulus is stronger at step 625 (i.e., the odorize stimulus or neutral stimulus), that same odorant pair is delivered 630 to the test subject a second time. Again, the test subject is prompted to indicate which stimulus of the pair was stronger.

If the stronger stimulant is again correctly identified, a fourth pair of stimuli are delivered 635 to the test subject. The fourth pair of stimuli includes one odorized stimulus having a weaker intensity of n-butanol (i.e., weaker than the intensity of the odorized stimuli delivered at steps 625, 630) and one neutral stimulus. After delivering the fourth pair of stimuli, the olfactory testing device prompts the test subject to indicate which stimulus of the pair was stronger. If the user correctly identifies which stimulus is stronger at step 635 (i.e., the odor stimulus or neutral stimulus), that same odorant pair is delivered 640 to the test subject a second time. Again, the test subject is prompted to indicate which stimulus of the pair was stronger.

The method of FIG. 6 starts with the highest intensity of n-butanol. In some approaches, if in the beginning, the test subject misses four presentations of the most intense n-butanol, the program automatically stops. In accordance with the method of FIG. 5, the olfactory testing device may perform the above method using phenylethylamine (PEA) instead of n-butanol.

FIG. 7 is a process flow diagram for an exemplary odor discrimination test 700. The odor discrimination test 700 may be conducted using the olfactory testing device of FIG. 2. With reference to FIG. 7, the odor sensitivity threshold test may begin when the olfactory testing device receives 705 an input indicative of the odor discrimination test selection. The olfactory testing device may receive the input, for example, via a user interface on the electronic display of the olfactory testing device. In some approaches, a test subject may select the odor sensitivity threshold test by pressing a button on the user interface.

Next, the olfactory testing device may instruct 710 the test subject to connect a nose piece of the olfactory testing device to his or her nose. In some approaches, the olfactory testing device instructs 710 the test subject via a message presented via the user interface on the electronic display of the olfactory testing device.

The olfactory testing device then selects 715 a sequence of odor pairs to be presented to the test subject using a random selection algorithm. In some approaches, software random number generations (RNG) may be generated for all of the odorants repeatedly and numbers are ordered. The two lowest numbers may then be paired. This may be repeated for every odor pairing in the sequence. The RNG may use mathematical algorithms to generate random numbers, initializing the algorithm with a "seed" value derived from some repetitive operation in the computer, such as keystrokes, a device's clock, or mouse movements. In other approaches, a hardware random number generation may be used, in which "seed" values are not required for initialization. In some approaches, the random selection algorithm randomly selects between three odors with a similar attribute (e.g., fruit attribute, savory attribute). In some approaches, the sequence may include 20 odor pairs including about 10 dissimilar odor pairs and about 10 similar odor pairs.

The olfactory testing device delivers 720 the selected sequence of odor pairs to the test subject. In some approaches, the olfactory testing device presents each odor to the test subject for about 15, 10, 5, 4, 3, or 2 seconds. To present each odor, the olfactory testing device may, for example, disperse one or more puffs of air containing an odorant. The olfactory testing device may present an odor pair about every 20, 15, 10, or 5 seconds, with about a 5, 4, 3, or 2 second interval between the first odor in the pair and the second odor in the pair. In some examples, an equal number of concordant and discordant odors may be selected and presented to a test subject. In one example, the olfactory testing device may select and present the following sequence of odorant pairs: Odor 1-Odor 1; Odor 1-Odor 3; Odor 2-Odor 1; Odor 3-Odor 2; Odor 2-Odor 2.

After presenting each odor pair in the sequence, the olfactory testing device prompts 725 the test subject to identify whether the first and second odor in the odor pair are the same or different (i.e., prompts the test subject to provide odor pair discrimination results). In one approach, the olfactory testing device may prompt a test subject to select "Yes" if the two odors in the odor pair are the same and to select "No" if the two smells in the odor pair are different. The olfactory testing device then receives 730 an answer (i.e., odor pair discrimination results) from the test subject, for example via a user interface of the olfactory testing device, and optionally may store 735 the odor pair identification results.

Next, the olfactory testing device compares 740 the odor pair discrimination results received from the test subject to the actual odor pair. That is, the olfactory testing device compares the test subject's answer regarding whether the odor pair is the same or different to whether the actual odor pair was the same or different. The olfactory testing device performs this comparison for each odor pair in the sequence. The olfactory testing device then computes 745 an odor discrimination score for the test subject based on the comparison of odor pair discrimination results to the actual odor pairs. The odor discrimination score is the total number of correct answers provided by the test subject out of the total number of odor pairs presented in the sequence. For example, when the sequence includes a total of 20 odor pairs, the odor discrimination score is presented as a fraction or percentage of 20.

Optionally, after computation of the final odor discrimination score, the olfactory testing device may present the score or other test results to the test subject via the electronic display of the olfactory testing device. In one example, results information may be presented to a test subject in the form of raw and normative scores on odor discrimination, by age, sex, ethnicity, and other demographic variables.

In some forms, all odorants used for odor threshold and odor discrimination tests may be included in a single cartridge. In other forms, all odorants used for odor threshold and odor discrimination tests may be included in separate cartridges for each test. Odor threshold test methods may be used to screen for viral infections that affect the smell receptors in the nose, such as the SARS-COV2 (COVID-19) virus and herpes viruses. Odor discrimination test methods may be used to screen for infections and diseases that affect the parts of the brain that process smell information coming from the nose, for instance COVID-19 infection that has spread to the brain, concussion involving the brain regions, and neurodegenerative diseases like Alzheimer's and Parkinson's disease.

In some forms, the olfactory testing device may also be capable of conducting odor memory and identification tests. In this form, the device may include a cartridge that houses up to about 20 odorants to facilitate testing for odor memory and identification.

It is contemplated that the olfactory testing devices and methods provided herein may be used as to test olfactory function to screen individuals for various illnesses that may impair olfactory function, such as COVID-19. For example, an odor threshold sensitivity test and/or an odor discrimination test may be administered to screen a patient suspected of having COVID-19. In this manner the devices and methods provided herein may be useful to detect hyposmia or anosmia in patient suspected of having COVID-19. In addition, as part of a COVID-19 screening protocol, the olfactory testing device may collect information on the presence or absence of systemic body symptoms (including but not limited fever, cough, sore throat, fatigue, diarrhea, loss of taste, and loss of appetite) and uses linear and nonlinear computational algorithm to compute risks of COVID-19.

Example 1

The olfactory testing device described herein (see FIG. 1) was used to conduct odor threshold sensitivity tests and odor discrimination tests on fifteen test subjects. The fifteen test subjects (31-44 years old, 60% females) had no nasal or neurological diseases. Each test subject completed odor threshold tests using the odor threshold sensitivity test described with reference to FIGS. 5 and 6, an Olfact-Combo Olfactometer (see Nwulia E A, Rai N, Sartip K, et al. A Pilot Study of Reduced Olfactory Bulb Volume as a Marker of PTSD in Childhood Trauma-Exposed Adult HIV-Infected Patients, J Trauma Stress, 2017; 30(5):537-544), and Sniffin' Sticks (Kobal G, Hummel T, Sekinger B, Barz S, Roscher S, et al. "Sniffin' sticks": screening of olfactory performance, Rhinology 1996; 34:222-226). Inter-test correlations were measured and are presented in Table 1.

TABLE 1

Inter-test Correlations in Odor Threshold Sensitivity Scores Obtained Through 3 Means: (1) PEA and N-Butanol Weighted Threshold, (2) Olfact-Combo Olfactometer, (3) Sniffin' Sticks

|  | PEA/N-Butanol Threshold | Olfact: Threshold | Sniffin' Sticks: Threshold |
|---|---|---|---|
| PEA/N-Butanol Threshold | 1.00 |  |  |
| Olfact-Combo: Threshold | 0.91*** | 1.00 |  |
| Sniffin' Sticks: Threshold | 0.88*** | 0.77** | 1.00 |

*is P value < 0.05; is P value < 0.01; *is P value < 0.0001

The correlations in Table 1 show strong correlations between odor threshold scores from the combination PEA/N-Butanol odor threshold sensitivity test compared with threshold scores from the Olfact-Combo Olfactometer and Sniffin' Sticks.

Example 2

The odor threshold sensitivity test of FIGS. 5 and 6 was administered to twelve test subjects. The test subjects were asymptomatic (age 28-41, 58% males, all clinicians) received COVID-19-positive RNA results within four weeks of odor testing but received COVID-19-negative RNA results within 4 days of odor testing, while antibody positive. The test subjects were also compared to age- and sex-matched people with negative COVID-19 genetic and antibody tests. For comparison, odor identification tests (i.e., a 40-item smell test and an olfactometer test) were also conducted on the test subjects. Data comparing test results for COVID-19 and non-COVID-19 test subjects are presented in Table 2.

TABLE 2

Odor Threshold Tests Compared to Odor Identification Tests in COVID-19 and Non-Covid-19 Test Subjects

| ID | COVID Positive | PEA/N-Butanol Weighted Threshold | 40-item Smell Test: Identification Score: | Olfactometer: 20-Item Identification Score |
|---|---|---|---|---|
| 1 | yes | 1.5*** | 24‡ | 7‡ |
| 2 | yes | 3.5* | 30‡ | 10‡ |
| 3 | yes | 4* | 33‡ | 12‡ |
| 4 | yes | 3** | 33‡ | 12‡ |
| 5 | yes | 1.5*** | 28‡ | 10‡ |
| 6 | yes | 5* | 38 | 13‡ |
| 7 | yes | 2.5** | 34‡ | 18 |
| 8 | yes | 5* | 38 | 18 |
| 9 | yes | 3** | 34‡ | 16 |
| 10 | yes | 3.5** | 32‡ | 13‡ |
| 11 | yes | 5.5* | 39 | 19 |
| 12 | yes | 4* | 33‡ | 13‡ |
| 13 | no | 9.5 | 38 | 16 |
| 14 | no | 10 | 40 | 20 |
| 15 | no | 9 | 40 | 19 |
| 16 | no | 8.5 | 37 | 20 |
| 17 | no | 10 | 38 | 17 |
| 18 | no | 5.5* | 33‡ | 9‡ |

For Threshold Score: *, , and * indicate >1.96, >2.5, and >3.0 standard deviations less than expected score.
For the other tests, ‡ indicates reduced performance As illustrated in Table 2, all asymptomatic COVID-19 test subjects score 1.96 standard deviations less than expected for the odor threshold score. However, the 40-item odor identification test identified impairments in 75% of asymptomatic COVID-19 test subjects, while the 20-item olfactometer tests identified 67% of asymptomatic COVID-19 test subjects. The data in Table 2 also illustrates that identification tests identifies all symptomatic tests subjects that have profound smell loss (i.e., anosmia), and only dies not detect those with milder odor sensitivity loss.

Example 3

A COVID-19 screening is conducted using the olfactory testing device of FIG. 2. The olfactory testing device of FIG. 2 is provided to a test subject suspected of having COVID-19. The test subject selects COVID-19 via the user interface of the olfactory testing device. Next, the olfactory testing device executes the testing protocol for odor threshold sensitivity using the method of FIGS. 5 and 6. The testing device also prompts the test subject to answer questions/input information regarding other symptoms including fever, cough, sore throat, fatigue, diarrhea, loss of taste, and loss of appetite.

Each symptom is assigned score of 0.5, while odor threshold is scored by standard deviations below the expected score. The test subject indicated having fever, sore throat and had an odor threshold score 3 standard deviations below mean for odor threshold. Thus, the test subject's COVID-19 test score is calculated to be 0.5+0.5+3.0=4. In the COVID-19 test screening, anyone with >1.96 score on odor threshold and has at least one of the other COVID-19 symptoms above is suspicious and recommended to do a diagnostic COVID-19 test. Accordingly, the test subject is recommended for a diagnostic COVID-19 test.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A method of testing an odor threshold sensitivity of a test subject using an olfactory testing device, the olfactory testing device comprising a pneumatic system operable to deliver stimulants to the test subject and a user interface to receive input from the test subject, the method comprising:

receiving input at the user interface of the olfactory testing device to perform an odor threshold sensitivity test; and in response to the input to perform the odor threshold sensitivity test, performing the odor threshold sensitivity test at the olfactory testing device including:

conducting staircase reversals using n-butanol including operating the pneumatic system to deliver n-butanol test stimulants to the test subject and receiving n-butanol test input from the test subject via the user interface;

computing an n-butanol odor threshold sensitivity score using data from the staircase reversals using n-butanol;

conducting staircase reversals using phenylethylamine including operating the pneumatic system to deliver phenylethylamine test stimulants to the test subject and receiving phenylethylamine test input from the test subject via the user interface;

computing a phenylethylamine odor threshold sensitivity score using data from the staircase reversals using phenylethylamine; and computing a final odor threshold sensitivity score using the n-butanol odor threshold sensitivity score and the phenylethylamine odor threshold sensitivity score, wherein the final odor threshold sensitivity score is the mean of the n-butanol and phenylethylamine odor threshold sensitivity scores.

2. The method of claim 1, wherein the staircase reversals using n-butanol comprises:

delivering a first pair of stimuli including a first neutral air stimulus and a first odorized air stimulus comprising n-butanol via the pneumatic system of the olfactory testing device;

prompting the test subject via the user interface to indicate which stimulus in the first pair is stronger;

where the test subject correctly indicates which stimulus in the first pair is stronger, delivering a second pair of stimuli including a second neutral air stimulus and a second odorized air stimulus comprising n-butanol via the pneumatic system of the olfactory testing device, wherein the second odorized air stimulus has a lower odor intensity of n-butanol than the first odorized stimulus, prompting the test subject via the user interface to indicate which stimulus in the second pair is stronger;

where the test subject does not correctly indicate which stimulus in the second pair is stronger, delivering a third pair of stimuli including a third neutral air stimulus and a third odorized air stimulus comprising n-butanol via the pneumatic system of the olfactory testing device, wherein the third odorized air stimulus has a higher odor intensity on n-butanol than the second odorized stimulus.

3. The method of claim 1, wherein the staircase reversals using phenylethylamine comprises:

delivering a first pair of stimuli including a first neutral air stimulus and a first odorized air stimulus comprising phenylethylamine via the pneumatic system of the olfactory testing device;

prompting the test subject via the user interface to indicate which stimulus in the first pair is stronger;

where the test subject correctly indicates which stimulus in the first pair is stronger, delivering a second pair of stimuli including a second neutral air stimulus and a second odorized air stimulus comprising phenylethylamine via the pneumatic system of the olfactory testing device, wherein the second odorized air stimulus has a lower odor intensity of phenylethylamine than the first odorized stimulus, prompting the test subject via the user interface to indicate which stimulus in the second pair is stronger;

where the test subject does not correctly indicate which stimulus in the second pair is stronger, delivering a third pair of stimuli including a third neutral air stimulus and a third odorized air stimulus comprising phenylethylamine via the pneumatic system of the olfactory testing device, wherein the third odorized air stimulus has a higher odor intensity of phenylethylamine than the second odorized stimulus.

4. The olfactory testing device of claim 1 wherein the olfactory testing device includes one or more stimulant chambers and the pneumatic system of the olfactory testing device includes an air pump and one or more valves associated with each of the one or more stimulant chambers, wherein conducting staircase reversals using n-butanol includes changing a state of the one or more valves and operating the air pump to cause air to flow through the one or more stimulant chambers to the test subject, wherein conducting staircase reversals using phenylethylamine includes changing the state of the one or more valves and operating the air pump to cause air to flow through the one or more stimulant chambers to the test subject.

5. The olfactory testing device of claim 4 wherein the pneumatic system of the olfactory testing device includes a neutral air conduit bypassing the one or more stimulant chambers, wherein conducting staircase reversals using n-butanol includes changing the state of the one or more valves and operating the air pump to cause air to flow through the neutral air conduit to the test subject, wherein conducting staircase reversals using phenylethylamine includes changing the state of the one or more valves and operating the air pump to cause air to flow through the neutral air conduit to the test subject.

* * * * *